(12) United States Patent
Mullen et al.

(10) Patent No.: US 6,689,055 B1
(45) Date of Patent: Feb. 10, 2004

(54) METHOD AND APPARATUS FOR ACQUISITION AND ANALYSIS OF NON-IMAGING DATA COLLECTED DURING ULTRASOUND EXAM

(75) Inventors: Paul Mullen, Waukesha, WI (US); Gregory C. Stratton, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/476,596

(22) Filed: Dec. 31, 1999

(51) Int. Cl.⁷ ................................................ A61B 5/00
(52) U.S. Cl. ........................... 600/300; 600/437; 705/2
(58) Field of Search ................................. 600/437, 443, 600/371, 439; 73/583; 345/708, 781, 808, 810; 378/118; 455/563; 702/184; 705/3; 379/88.01; 235/375, 385

(56) References Cited

U.S. PATENT DOCUMENTS

| | | | |
|---|---|---|---|
| 4,646,261 A | | 2/1987 | Ng ............................. 364/900 |
| 5,315,999 A | * | 5/1994 | Kinicki et al. .......... 128/660.07 |
| 5,544,654 A | * | 8/1996 | Murphy et al. ......... 128/660.07 |
| 5,563,607 A | * | 10/1996 | Loomis et al. ............... 342/357 |
| 5,615,678 A | * | 4/1997 | Kirkham et al. ........ 128/660.01 |
| 6,064,979 A | * | 5/2000 | Perkowski .................... 705/26 |
| 6,065,138 A | * | 5/2000 | Gould et al. .................. 714/47 |
| 6,108,493 A | * | 8/2000 | Miller et al. ........... 395/200.49 |

FOREIGN PATENT DOCUMENTS

WO    WO 98/24358    6/1998

* cited by examiner

Primary Examiner—Francis J. Jaworski
(74) Attorney, Agent, or Firm—Ostrager Chong & Flaherty LLP

(57) ABSTRACT

A method and a system for acquiring and analyzing non-imaging data collected during an ultrasound examination for the purpose of reporting ultrasound department performance characteristics. This is accomplished by tracking user keystrokes whenever the ultrasound imaging system is turned on, acquiring the keystroke data from the ultrasound system and then using this data for departmental performance analysis. During an examination, the ultrasound system user presses buttons and selects items from menus on the operator interface. These keystrokes invoke functions or change operating parameters on the ultrasound imaging system. Simultaneously, a code representing the keystroke is stored in electronic storage. Along with this code, the date, time and values being set or adjusted are also stored. Subsequently, the data in the electronic storage can be extracted for use in analysis of the use of the ultrasound imaging system.

43 Claims, 8 Drawing Sheets

METHOD AND APPARATUS FOR ACQUISITION AND ANALYSIS OF NON-IMAGING DATA COLLECTED DURING ULTRASOUND EXAM

FIELD OF THE INVENTION

The present invention relates generally to the operation of an ultrasound imaging system. In particular, the invention relates to methods for measuring productivity within a department which performs ultrasound examinations.

BACKGROUND OF THE INVENTION

Ultrasound imaging systems are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by service centers capable of contacting scanners at subscribing institutions directly without the need for intervention on the part of the institution personnel. Such centralized servicing is intended to maintain the ultrasound imaging system in good operational order without necessitating the attention of physicians or radiologists, and is often quite transparent to the institution.

In certain centralized servicing systems, a computerized service center may contact a scanner via a network to check system configurations and operational states, to collect data for report generation, and to perform other useful service functions. Such contacts can be made periodically, such as during system "sweeps", in which a variety of system performance data is collected and stored with historical data for the particular scanner. The data can then be used to evaluate system performance, propose or schedule visits by service personnel, and the like.

In addition, currently available service systems also permit some degree of interaction between service centers and institutions. For example, an interactive service system is known which facilitates valuable exchanges of information, including reports of system performance, feedback on particular incidents requiring attention, updates of system licenses, software, imaging protocols, etc. In particular, a platform has been developed that allows a central service facility to exchange information on possible service problems with remotely located scanners, and to retrieve information or data log files from scanners for the purpose of servicing those scanners.

Within a department having one or more ultrasound imaging systems operated by one or more system operators, it is important to make efficient usage of the available equipment. In the case where multiple technicians having different skill levels operate the same equipment, it would be desirable to monitor operator performance during an ultrasound examination. Preferably the central service facility would extract data from the remote ultrasound imaging systems in a department, perform an analysis of ultrasound department performance characteristics, and then download a performance report to the department manager at the remote facility. Alternatively, a field service engineer visiting the remote site would be able to extract the same data and generate the same report.

SUMMARY OF THE INVENTION

The present invention is directed to a method and a system for acquiring and analyzing non-imaging data collected during an ultrasound examination for the purpose of reporting ultrasound department performance characteristics. In accordance with the preferred embodiments of the invention, this is accomplished by tracking user keystrokes whenever the ultrasound imaging system is turned on, acquiring the keystroke data from the ultrasound system and then using this data for departmental performance analysis. As used herein, the term "keystroke" includes operation of input devices on the operator interface or on an ultrasound probe, the selection of menu items on a graphical user interface, as well as the act of plugging in a probe or lifting a probe off of its yoke.

During an examination, the ultrasound system user presses buttons and selects items from menus on the operator interface. These keystrokes invoke functions or change operating parameters on the ultrasound imaging system. Simultaneously, a code representing the keystroke is stored in electronic storage. Along with this code, the date, time and values being set or adjusted are also stored. This information is preferably saved in long-term storage, so that many days worth of "keystroke logs" can be analyzed.

Subsequently, the data in the electronic storage can be extracted for use in analysis of the use of the ultrasound imaging system. The analysis can take place at a central service facility or off-line in other computational equipment at the remote site. Alternatively, the analysis could be performed on the ultrasound imaging system itself. In the latter case, a system controller could be programmed with keystroke analysis software.

In accordance with the preferred embodiment of the invention, the keystroke data is sorted, filtered and then reported in spreadsheet, chart or other formats. In particular, the data, when extracted, can be sorted to determine productivity measurements such as: (1) the number of exams performed by type, day operator, referring physician, etc.; (2) the length of time of exams, individually, collectively, or by specific type; (3) a comparison of the productivity of individual operators; (4) conformance to departmental processes and procedures (useful for quality system validation); and (5) a determination of the key factors affecting departmental productivity. The invention is not limited to these examples of productivity measurements which can be made.

In accordance with the preferred embodiment of the invention, a central service facility acquires keystroke data from one or more remotely located ultrasound imaging systems via a network. The system controller of the ultrasound imaging system is programmed to store encoded keystroke data whenever the system is turned on. A keystroke analysis server at the central service facility is programmed to retrieve the stored keystroke data from one or more selected ultrasound imaging systems. The acquired keystroke data is then sorted and filtered in accordance with a keystroke analysis routine. Then appropriate reports can be generated for use by the service facility or by the remote facility if the contract or subscription with the latter provides for such reporting.

In accordance with one preferred embodiment, a system comprises a central service facility connected to a multiplicity of remotely located ultrasound imaging systems via a network. Each imaging system comprises: means for storing keystroke data; means for transmitting the keystroke data to the network addressed to the service facility; and means for receiving a performance analysis from the network. The service facility comprises: means for receiving the keystroke data via the network; means for analyzing the keystroke data; means for generating a report of performance analysis results; and means for transmitting the report to the network addressed to the ultrasound imaging system. Alternatively, the report can be sent to an administrative workstation at the remote facility instead of to the ultrasound imaging system itself.

In accordance with another preferred embodiment, the keystroke analysis may be performed at a workstation which is located at the remote site and which communicates with one or more ultrasound imaging systems via a local area network. Alternatively, the workstation for performing keystroke analysis may be a standalone station, with the keystroke data being conveyed by storing the keystroke data on a disk at the ultrasound imaging system and then physically conveying the disk to the workstation.

In accordance with an alternative preferred embodiment, the system controller of the remote ultrasound imaging system can be programmed to analyze its own keystroke data. There are, however, limitations on available processing power and the ability to compare the results to the results of other similarly situated systems.

DETAILED DESCRIPTION OF THE PREFERRED EMBODIMENTS

In accordance with the preferred embodiments of the invention, keystroke data is stored in electronic memory during operation of an ultrasound imaging system. Examples of "keystrokes" which are input to an ultrasound imaging system in accordance with the preferred embodiments are described with reference to FIGS. 1–4.

Figure 1:
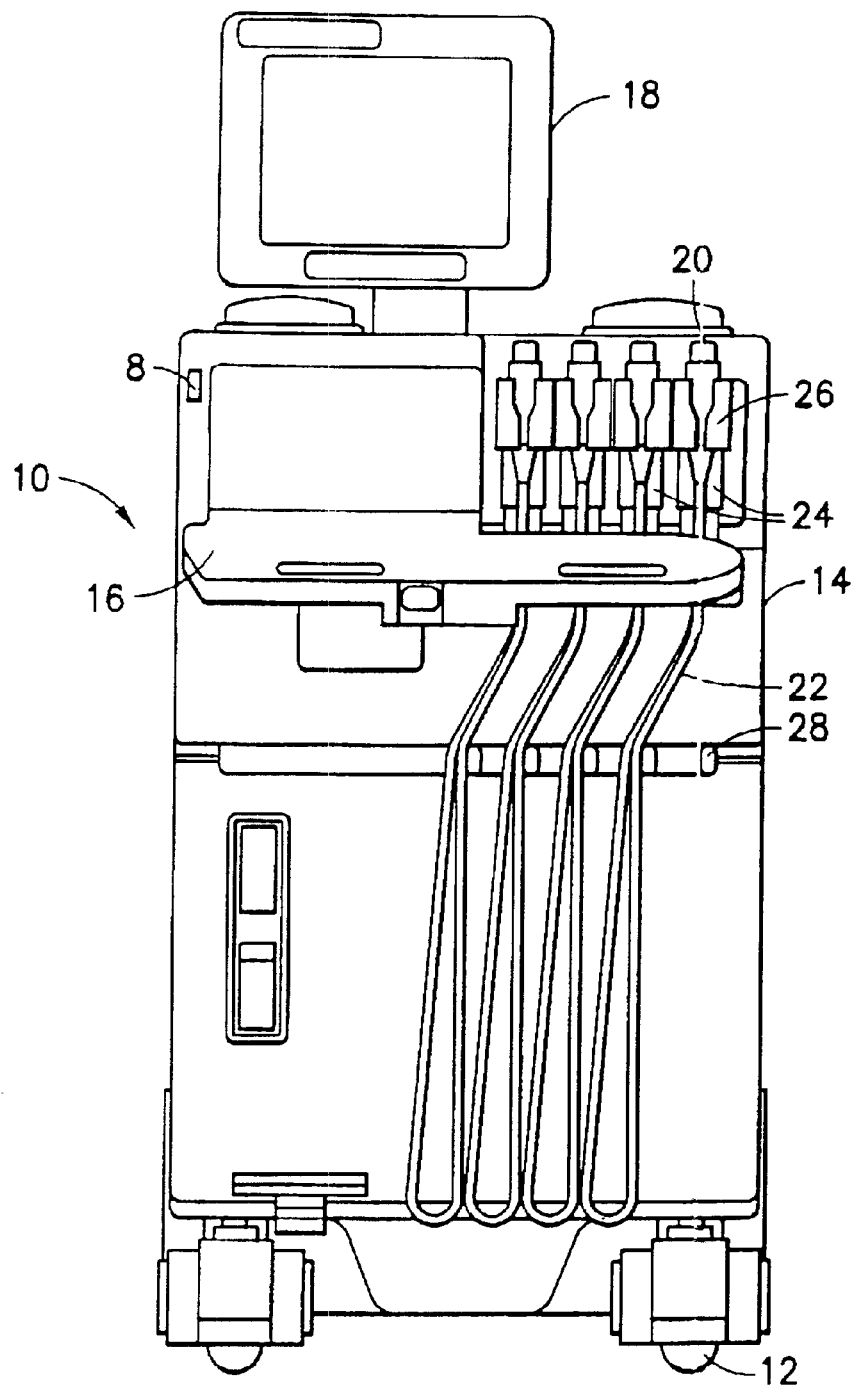
FIG. 1 is a schematic showing a front view of an ultrasound imaging system having a plurality of interchangeable probe assemblies.

FIG. 1 shows an ultrasound imaging system having a plurality of interchangeable transducer probes. The system comprises a mobile main unit 10 which is transportable on a plurality of wheels 12. The main unit includes a housing 14, an operator panel 16 and a display monitor 18. The housing 14 has a plurality of ports (not shown) by means of which a plurality of transducer probes 20 can be coupled to the signal processing subsystems located inside housing 14.

Typically each probe is designed to meet the requirements of a specific application. The transducers fall into four general categories: phased array, linear, convex and specialty (i.e., transducers designed for imaging specific body parts).

Each transducer probe is coupled to a respective port of the ultrasound imaging system via a coaxial cable 22 and a transducer connector 24. The transducer connectors are interchangeable in the sense that each connector can be plugged into any port. A set of yokes 26 are provided for holding the respective transducers when they are not being used, as shown in FIG. 1. Each yoke is attached to a corresponding transducer connector. The transducer probe, coaxial cable, connector and yoke form a transducer probe assembly. If the operator wishes to connect a different probe to the system, an entire probe assembly is removed and replaced by the new probe assembly.

Figure 2:
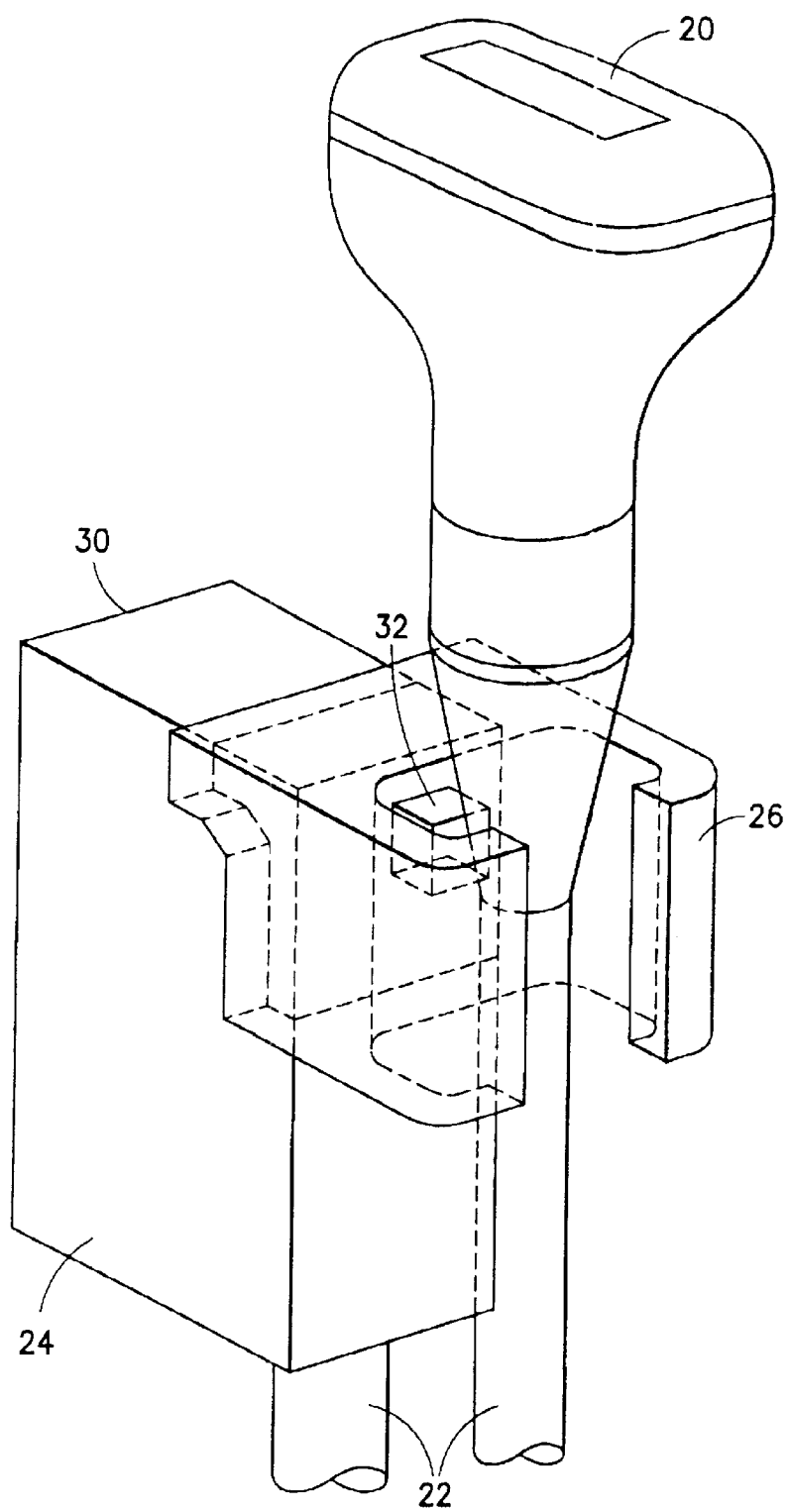
FIG. 2 is a block diagram of a transducer interface by which a transducer probe can be interfaced to an ultrasound imaging system.
Figure 3:
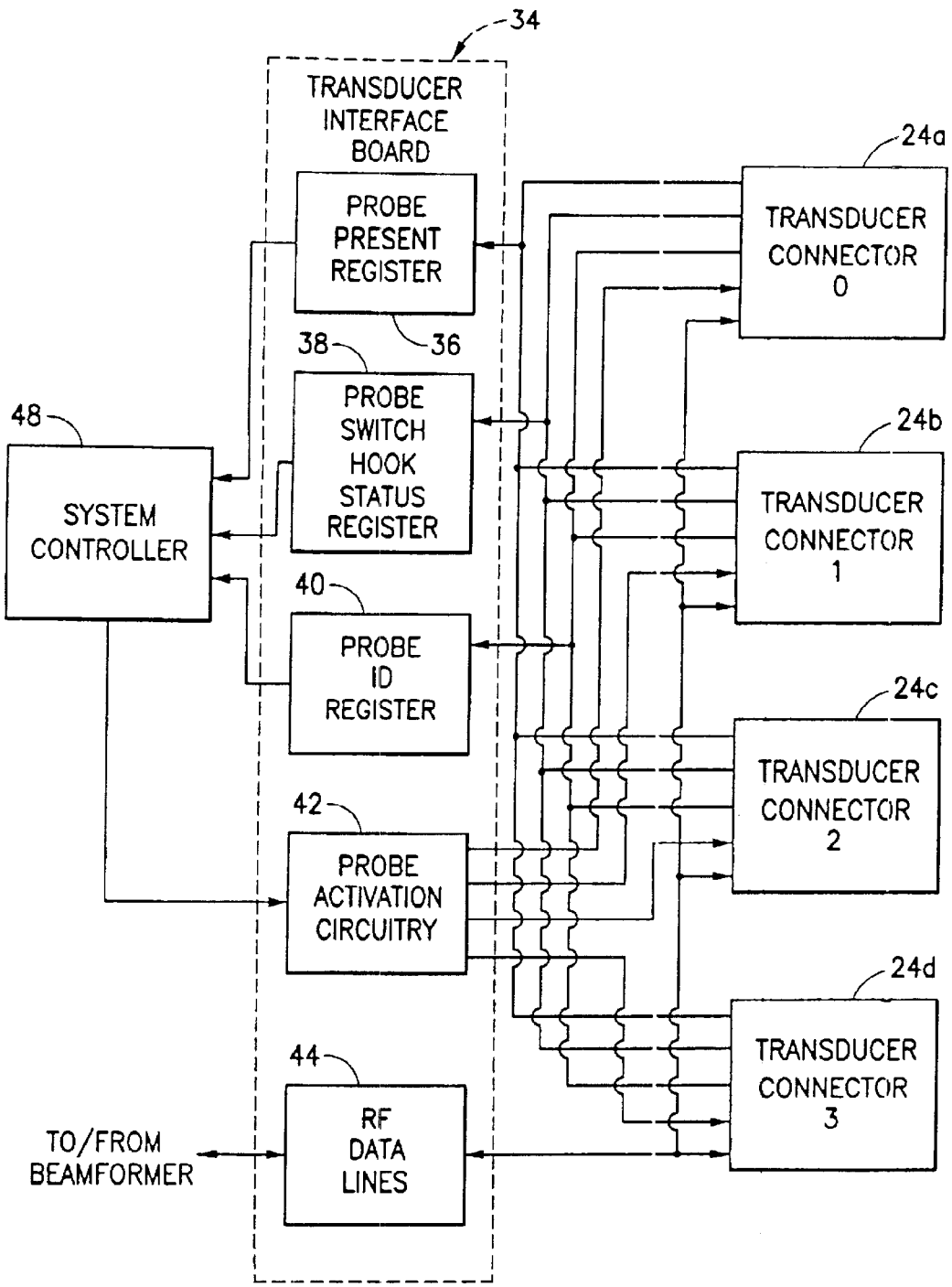
FIG. 3 is a concept drawing of a known integral yoke/transducer connector used in system shown in FIG. 1.

The structure of the integral yoke/transducer connector is shown in detail in FIG. 2. The transducer probe 20 has an array of transducer elements (not shown) which transmit ultrasound in a transmission mode and receive ultrasound echoes from the anatomy being examined in a reception mode. The signal electrodes of the transducer elements are electrically connected to one end of respective conductive wires (not shown) of the coaxial cable 22. The other end of the conductive wires of coaxial cable 22 are electrically connected to circuitry inside the connector box 30. The connector circuitry is in turn electrically connected to the port (not shown) in which it is plugged. That port is electrically connected to a transducer interface board (described in detail below with reference to FIG. 3).

A probe switch 32 is incorporated in the integral yoke/transducer connector. This probe switch functions as a means of telling the system when the probe 20 has been lifted out of the probe holder or yoke 26. The probe switch 32 supplies a simple "on" and "off" passive response (single pole, single throw). The switch is closed when the probe is of f the yoke and open when the probe is on the yoke. Each transition from an "on" to an "off" state and each transition from an "off" to an "on" state is deemed to be a "keystroke" for purposes of the present invention. Each such transition is encoded and stored in electronic memory.

The ultrasound imaging system utilizes the signal produced by the probe switch in determining the next transducer probe to be activated. In particular, a stack of probe identifiers, having an order which is determined by the order in which unactivated normal transducers attain a state of being both connected and out of their respective holder, is maintained by the system controller, which cooperates with the transducer interface 34 shown in FIG. 3. Up to four transducer probes can be connected to the imaging system via transducer connectors 2a–24d. When any one of the transducer connectors is plugged into a corresponding port in the imaging system, a Probe Present signal is produced which is stored in a probe present register 36.

As described above, each connector 24a–24d has a probe switch 32 (as shown in FIG. 2) for indicating whether the corresponding probe is coupled to the corresponding yoke. The resulting probe switch hook status signal is input into the system via a pin on the transducer connector. This pin is pulled high by a resistor on the transducer interface board 34. A transducer probe will either leave the pin floating, or ground the pin to form a signal indicating that the probe has been removed from its yoke. The resulting probe switch hook status signal is stored in a probe switch hook status register 38. In addition, each transducer type has a unique 8-bit probe ID code. The transducer connector has a respective pin for each bit of the probe ID code. These pins are pulled high by resistors on the transducer interface board 34. A transducer will either leave the pins floating, or ground them to form its unique probe ID. The probe ID signals are stored in a probe ID register 40. Depending on the contents of registers 36, 38 and 40, a system controller 48 outputs a Probe Select signal to the probe activation circuitry 42 on the transducer interface board 34. Probe activation circuitry 42 activates the selected transducer probe in response to that Probe Select signal.

A transducer selection control program is stored in system controller 48. The system controller periodically reads the contents of registers 36, 38 and 40 and processes the retrieved information in accordance with a stored algorithm to select a transducer for activation. The Probe Select signal sent to the probe activation circuitry 42 identifies the selected transducer. The selected transducer is activated by the probe activation circuitry 42 via the associated transducer connector. Radiofrequency data from the transducer element array is then multiplexed, under the control of the system controller, from the transducer connector to the beamforming circuitry (not shown) via the RF data lines 44 on the transducer interface board 34.

As should be apparent from the foregoing description, the system controller is able to detect which probe is active at each instant during system operation. In accordance with the preferred embodiment of the present invention, the time when a probe is activated (i.e., its probe switch undergoes a transition from the "on" to the "off" state) and the ID code for that activated probe are recorded electronically. Thus, the system maintains an electronic history evidencing which probes were used by the system operator during an examination. Subsequent analysis of that electronic data can reveal whether the system operator used the appropriate probe for a particular examination and the length of time each probe was activated.

In accordance with the preferred embodiment of the present invention, the system controller begins to record keystroke data as soon as the system power is turned on. Power is turned on by pushing switch 8 on the system console up. While the power is turned on, the system controller will record each probe activation (as previously described) as well as each operation of any other operator control during an examination. The other operator controls are located on the control panel 16, which is shown in detail in FIG. 4.

To start a new patient exam, the system operator presses the New Patient button 114 on the control panel. A New Patient menu is displayed on the monitor 18. The letter Y is typed to verify that the patient is new. Then the operator presses the Return button 116. The trackball 118 is then used to select the appropriate exam category from a list of exam categories which appears on the New Patient menu. The selection is made by pressing Set (by depressing button 120 on the control panel or clicking on a virtual Set button displayed on the New Patient menu). The selected exam category determines presets, available applications, and worksheets. The system operator then fills in appropriate patient data. Alternatively, for DICOM users, a worklist schedule can be displayed by pressing the ROI Size input device 122. The trackball 118 can be used to select a patient, following which the user presses Set. The New Patient menu appears with the data filled in. The user presses Exit (by depressing button 124 on the control panel or clicking on a virtual Exit button displayed on the New Patient menu) to quit. The user then selects the desired application. Operation of the Image Presets softkey 126 on the control panel selects, modifies, creates, archives, or views system or user presets. The user then selects the desired probe and begins scanning.

Figure 4:
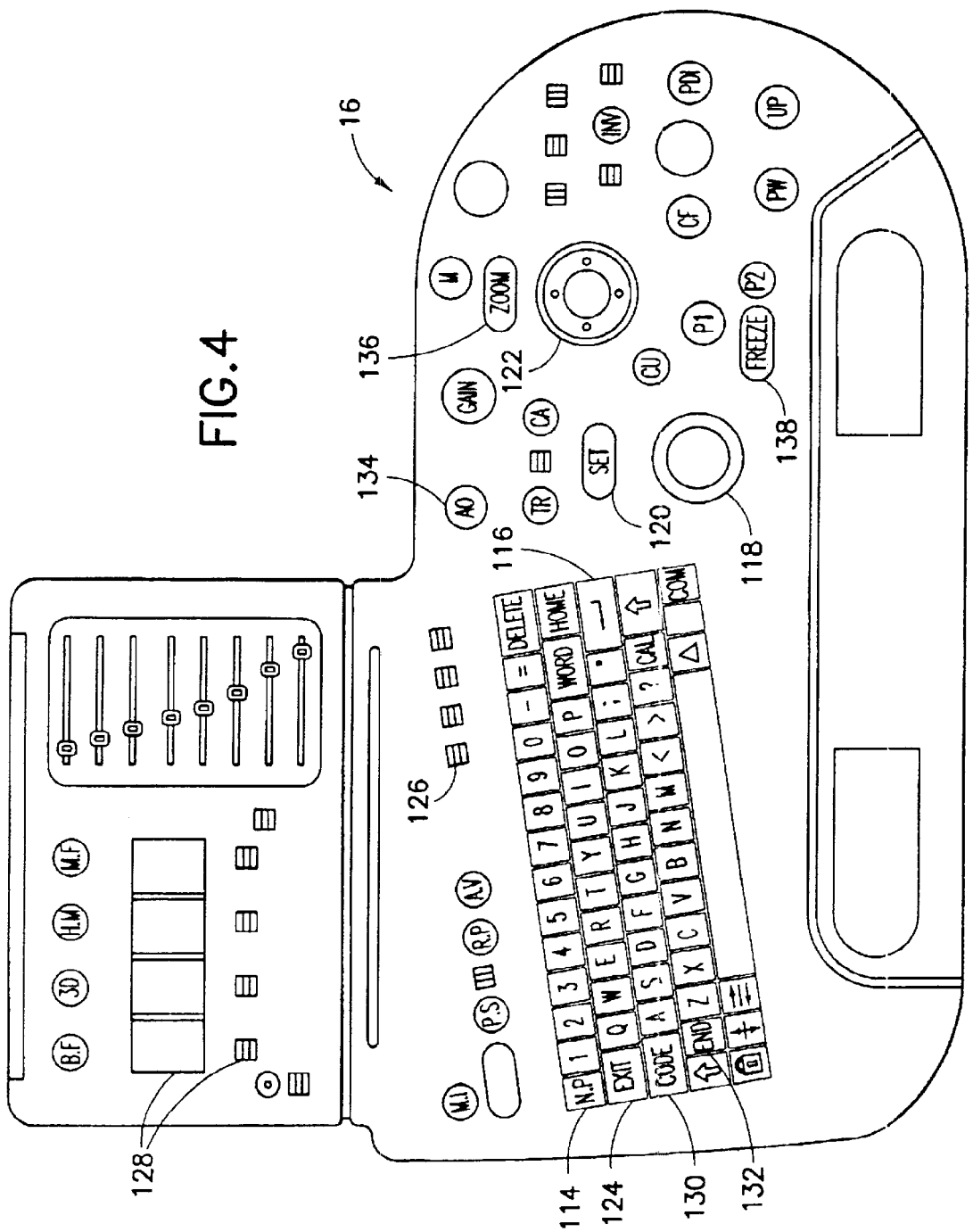
FIG. 4 is a schematic showing a typical control panel of a conventional ultrasound imaging system.

All of the foregoing keystrokes are time-stamped and encoded by the system controller, and the encoded keystroke data is stored in electronic memory. As shown in FIG. 4, the control panel is provided with a softkey display 128 and associated controls for displaying different menus as a function of the application being utilized. Pressing the Code key 130 plus a letter activates system features. Pressing the DICOM End Exam button 132 sends DICOM jobs to remotely located devices at the end of an exam. The Auto Optimize button 134 optimizes the image in B mode, color flow mode and Doppler mode. Pressing the Zoom button 136 magnifies the image. Activation of the Freeze button 138 freezes/unfreezes the image.

While the functionality of each and every key on the control panel will not be described here for the sake of economy, it should be appreciated that every keystroke is recorded in accordance with the method of the preferred embodiment. These keystrokes invoke functions or change operating parameters on the ultrasound imaging system. Simultaneously, a code representing the keystroke is stored in electronic storage. Along with this code, the date, time and values being set or adjusted are also stored. This information may or may not be saved through a system power cycle, however long-term storage is preferred.

Figure 5:
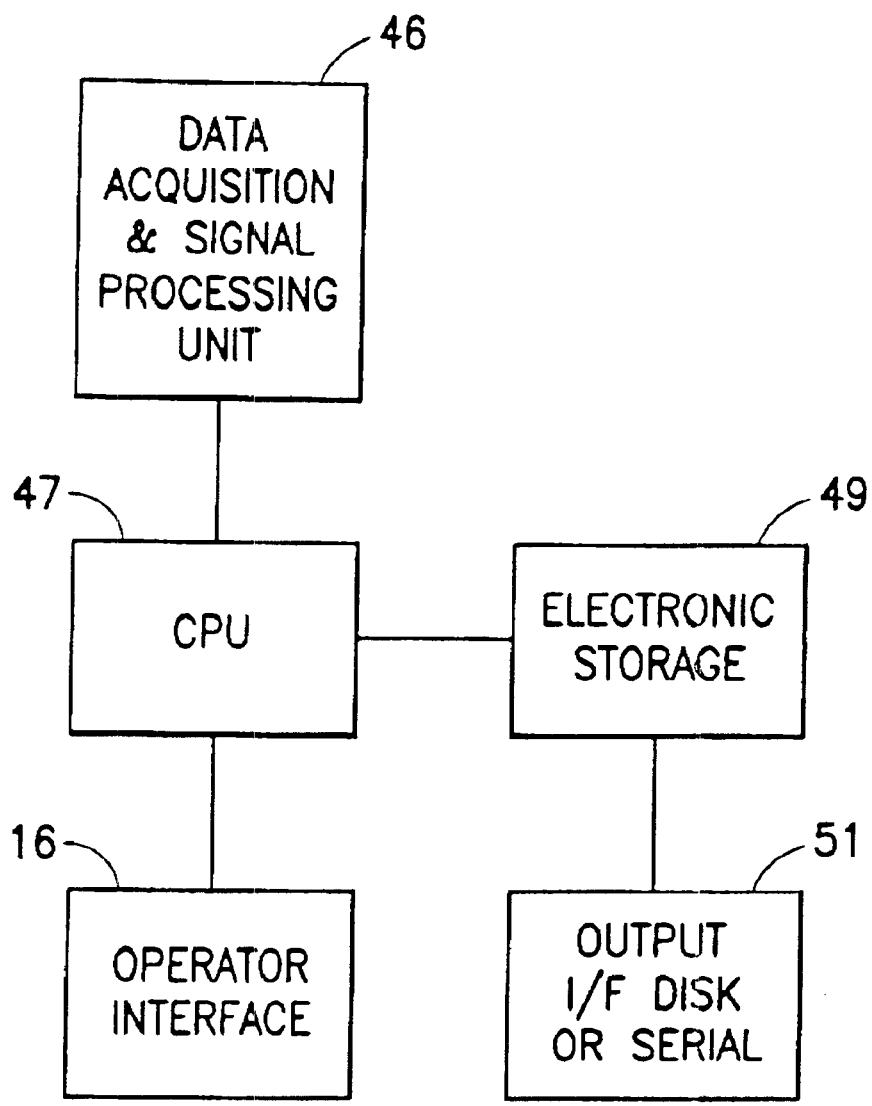
FIG. 5 is a block diagram showing an ultrasound imaging system in which keystroke data is stored in electronic memory.

Referring to FIG. 5, each ultrasound imaging system 2 comprises a data acquisition and signal processing unit 46 for transmitting ultrasound signals into a subject of interest, and for acquiring resultant signals which are processed for reconstructing a useful image. The system includes a system controller 48 which regulates operation of unit 46 and which processes acquired signals to reconstruct the image for display by a display monitor 18. The system controller preferably comprises a central processing unit 47 and associated system memory (electronic storage) 49. The system controller 48 can control the unit 46 to acquire data and process received signals in accordance with software stored in system memory and in accordance with various instructions input by a system operator via the control panel 16, which may include a keyboard, a mouse, a trackball and various other input devices, as previously described with reference to FIG. 4. The system controller is programmed with to encode every keystroke and to store encoded keystroke data in electronic storage 49. The ultrasound imaging system 2 also includes an output interface 51 for outputting the keystroke data to either a disk or a serial communication line. This allows the keystroke data in the electronic storage 49 to be extracted for use in analysis of the use of the ultrasound imaging system. The analysis can take place at a central service facility or off-line in other computational equipment at the remote site. Alternatively, the analysis could be performed on the ultrasound imaging system itself. In the latter case, the system controller 48 must be programmed with keystroke analysis software.

In accordance with the preferred embodiments of the invention, the keystroke data is sorted, filtered and then reported in spreadsheet, chart or other formats. In particular, the data, when extracted, can be sorted to determine productivity measurements such as: (1) the number of exams performed by type, day, operator, referring physician, etc.; (2) the length of time of exams, individually, collectively, or by specific type; (3) a comparison of the productivity of individual operators; (4) conformance to departmental processes and procedures (useful for quality system validation); and (5) a determination of the key factors affecting departmental productivity. The capability of determining the number of exams and/or computing the length of time of the exam make it possible to provide ultrasound imaging services to users on a cost-per-exam or cost-per-minute basis.

To accomplish the foregoing, processing/analysis tools are needed. In accordance with the preferred embodiment of the invention, the keystroke time-stamp logs generated by the ultrasound imaging system are stored in machine-readable binary form. In order to make the data useful to human decision-makers, the processing/analysis tools preferably provide four functions: data acquisition, data conversion, data aggregation, and data mining. [Optionally, the data acquisition and data aggregation can be eliminated in the case where the system controller of the ultrasound imaging system is itself able to perform keystroke analysis on its own keystroke data.]

In accordance with the preferred embodiment, the keystroke data is recorded and stored on the hard disk of the ultrasound imaging system as a normal part of the system's operating software. The data acquisition step involves transferring the data from the ultrasound imaging system to another computational platform (e.g., a personal computer at the remote site or a keystroke analysis server at a central service facility) for processing. This step can be implemented using networks (e.g., internet, intranet, and private networks) or using a sneaker-net diskette swap.

The keystroke data is stored in the ultrasound imaging system in machine-readable form. Each keystroke is stored with both its physical characteristics (which button pressed, at what time, in what direction (up, down, on, off, etc.) and its logical characteristics (what did it mean when the button was pressed). The first step in the data conversion strips out the physical characteristics, leaving just the time stamp and the meaning of the keystroke. In the second step (though it occurs at the same time as far as the operator is concerned), the data is converted into human-readable form. Generally this takes the form of an ASCII text document. Each document represents a single session on the ultrasound imaging system, from the time it is turned on to the time it is turned off.

The data aggregation step comprises the step of combining all of the data from each of the files collected in the data acquisition and data conversion processes. The data from multiple examinations, multiple sessions, multiple operators, and even multiple institutions are aggregated into a single database. From this point, data mining tools can be used to sort the data and make comparisons.

The data mining step makes use of statistical tools to collect and group data, to look for relationships, and to present the results. Grouping tools like histograms, relationship testing tools like T-tests, and data characterization tools such as mean, deviation, and normality tests are all used. The application of the tools changes from project-to-project depending on the mechanisms being tested for any particular situation.

In one example the customer had a "best" technician and wanted to know what made that technician the "best". Analysis of the keystroke data from the imaging system used by that technician demonstrate that he/she, in fact, was the fastest and most consistent system user. Furthermore, the analysis show that this technician handled the bulk of the examinations. When this data was correlated with probe use, it was discovered that the "best" technician was the only person on the staff who used a particular probe for the exam type being studied. This led to the customer making a policy change that required all users to use the same probe.

In accordance with another feature of the invention, the exam time could be computed based, e.g., on the time stamps associated with turning on and turning off of the power to an ultrasound imaging system. This computation is preferably done at a central service facility having billing capability. A bill for the use of the system could be automatically downloaded to the accounting department at the remote facility at regular billing intervals or after each exam.

In accordance with the preferred embodiment of the invention, a central service facility acquires keystroke data from one or more remotely located ultrasound imaging systems via a network. The system controller of the ultrasound imaging system is programmed to store encoded keystroke data whenever the system is turned on. A keystroke analysis server at the central service facility is programmed to retrieve the stored keystroke data from one or more selected ultrasound imaging systems at prescribed times. The acquired keystroke data is then sorted and filtered in accordance with a keystroke analysis routine. Then appropriate reports, e.g., in spreadsheet or chart form, can be generated for use by the service facility or by the remote facility if the contract or subscription with the latter provides for such reporting.

Figure 6:
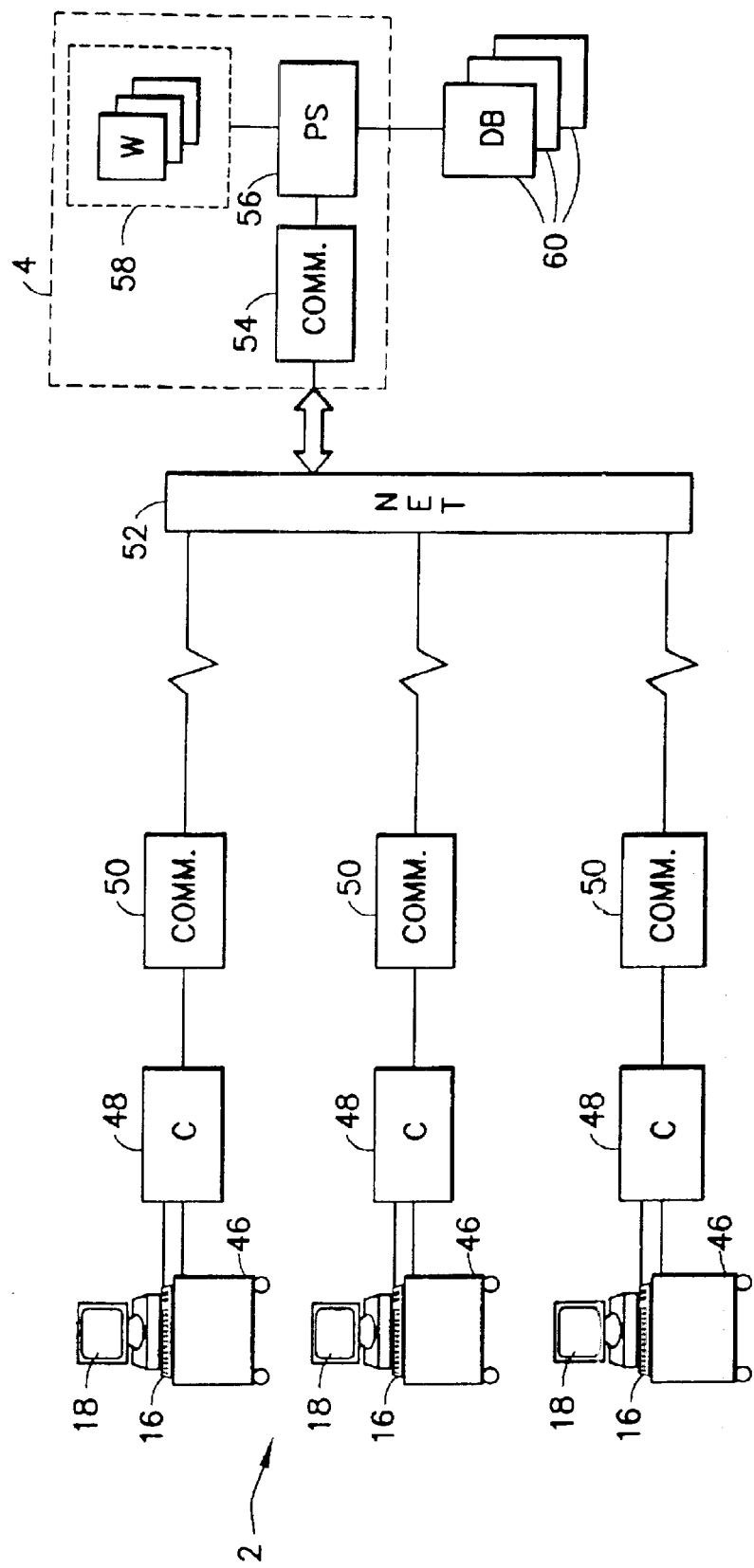
FIG. 6 is a diagrammatical representation of a plurality of remotely located ultrasound imaging systems coupled to a central service facility via a network connection for providing centralized analysis of keystroke data.

Referring to FIG. 6, a service system is illustrated for providing centralized service to a plurality of ultrasound imaging systems 2 located at different remote sites. The imaging systems are serviced from a centralized service facility 4 via a network 52, which may be an internet, an intranet, a local area network or any other network. Preferably, the central service facility 4 is able to extract keystroke data from each ultrasound imaging system via the network 52. In addition, the service facility 4 preferably comprises a processing system which is programmed with keystroke analysis software for analysis of keystroke data and automatic generation of departmental performance reports. Alternatively, the service facility is provided with workstations programmed with keystroke analysis software for enabling service personnel to analyze keystroke data and generate appropriate reports and charts.

Where more than one ultrasound imaging system is provided at a single facility or location, these may be coupled to a management station (not shown). The management station may be linked directly to controllers for the various imaging systems. The management system may include a computer workstation or personal computer coupled to the system controllers in an intranet configuration, a filesharing configuration, a client/server arrangement, or any other suitable arrangement. Such a management station would typically include a monitor for viewing system operational parameters, analyzing system utilization, and exchanging service requests and data between the remote facility and the central service facility. Alternatively, the management station could be programmed with keystroke analysis software.

Each communication module 50 may be linked to service facility 4 via a remote access network 52. For this purpose, any suitable network connection may be employed. Preferred network configurations include both proprietary or dedicated networks, as well as open networks, such as the Internet. Data may be exchanged between the ultrasound imaging systems 2 and central service facility 4 in any suitable format, such as in accordance with the Internet Protocol (IP), the Transmission Control Protocol (TCP), or other known protocols. Moreover, certain of the data may be transmitted or formatted via markup languages, such as the HyperText Markup Language (HTML), or other standard languages. The preferred interface structures and communications components are described in greater detail below.

Within service facility 4, messages, service requests and data are received by communication components as indicated generally at reference numeral 54. Components 54 transmit the service data (e.g., keystroke data) to a service center processing system, represented generally at reference numeral 56 in FIG. 6. The processing system 56 manages the receipt, handling and transmission of service data to and from the service facility. In general, processing system 56 may include one or a plurality of computers, as well as dedicated hardware or software servers for processing the various service requests and for receiving and transmitting the service data, as described more fully below. Service facility 4 also includes a bank of operator workstations 58, which may be staffed by service engineers who address the service requests and provide off- and on-line service to the diagnostic systems in response to the service requests. Also, processing system 56 may be linked to a system of databases or other processing systems 60 at or remote from the service facility 4. Such databases and processing systems may include extensive database information on operating parameters, service histories, etc., both for particular subscribing scanners and for extended populations of diagnostic equipment. As described below, such databases may be employed both for servicing of particular diagnostic systems and for tracking such servicing, as well as for deriving comparison data for use in servicing a particular system or a family of systems, or generating departmental performance reports.

Figure 7:
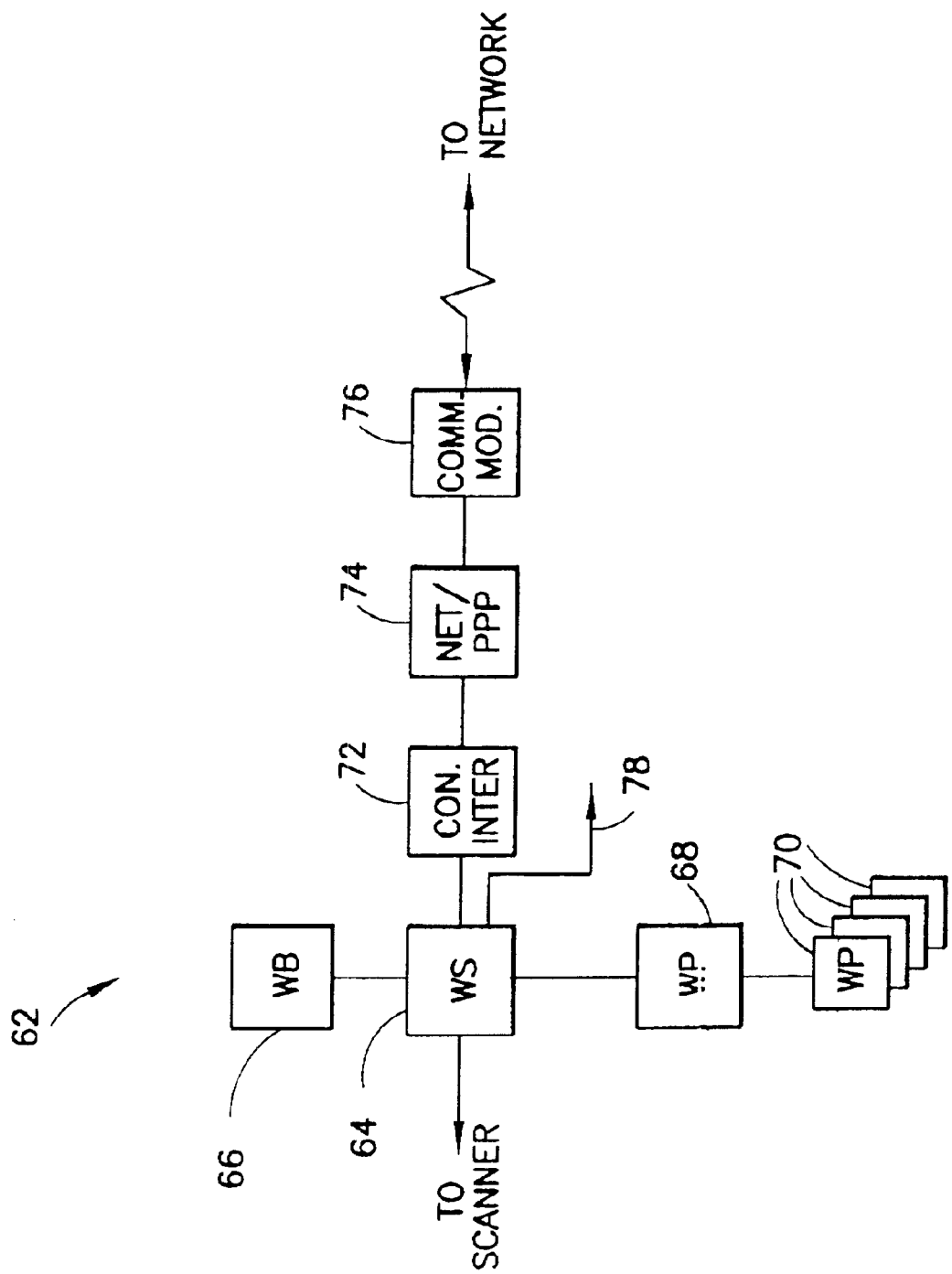
FIG. 7 is a block diagram of certain functional components within an ultrasound imaging system of the type shown in FIG. 1 for facilitating interactive centralized servicing of the ultrasound imaging system.

Within each ultrasound imaging system 2, a uniform service platform 62, shown in FIG. 7, is provided. Platform 62 includes hardware, firmware, and software components adapted for composing and transmitting service requests, transmitting and receiving service data, establishing network connections, and managing financial or subscriber arrangements between the remote system and the service facility. Preferably, the platform 62 is integrated into the system controller of the imaging system. These platforms provide a uniform graphical user interface at each imaging system. The platforms enable the service facility to interface directly with the control circuitry of the individual scanners, as well as with memory devices at the scanners, to access image, log (e.g., keystroke data) and similar files needed for rendering requested or subscribed services. Where a management station is provided, a similar uniform platform is preferably loaded on the management station to facilitate direct interfacing between the management station and the service facility.

FIG. 7 shows the various functional components comprising the uniform service platform 62 within each remote imaging system 2. This uniform service platform can be employed to facilitate the transmission of keystroke data from the remote system to the central service facility and the downloading of departmental performance reports from the service facility to the remote facility over a network. The uniform platform resides as software stored in a web server 64. Web server 64 facilitates data exchange between the imaging system and the service facility, and permits a series of web pages 68 and 70 to be viewed via a web browser 66. Preferably server 64 and browser 66 support HTTP applications and the browser supports Java applications. The main web page 68 is preferably a markup language page, such as an HTML page displayed for the system user on a monitor 18 of the display subsystem. Main web page 68 is preferably accessible from a normal operating page in which the user will configure examination requests, view the results of examinations, etc., such as via an on-screen icon. Through main web page 68, a series of additional web pages 70 are accessible. Such web pages permit service requests and requests for access to software applications to be composed and transmitted to the central service facility, and facilitate the exchange of other messages, reports, software, protocols, etc. The web server 64 communicates with a network via a modem 76. A connectivity service module 72 provides for interfacing with the web server 64. A Point-to-Point Protocol (PPP) module 74 is also provided for transmitting Internet Protocol (IP) packets over remote communication connections.

As will be appreciated by those skilled in the art, various other network protocols and components may be employed for facilitating data exchange over a network.

Figure 8:
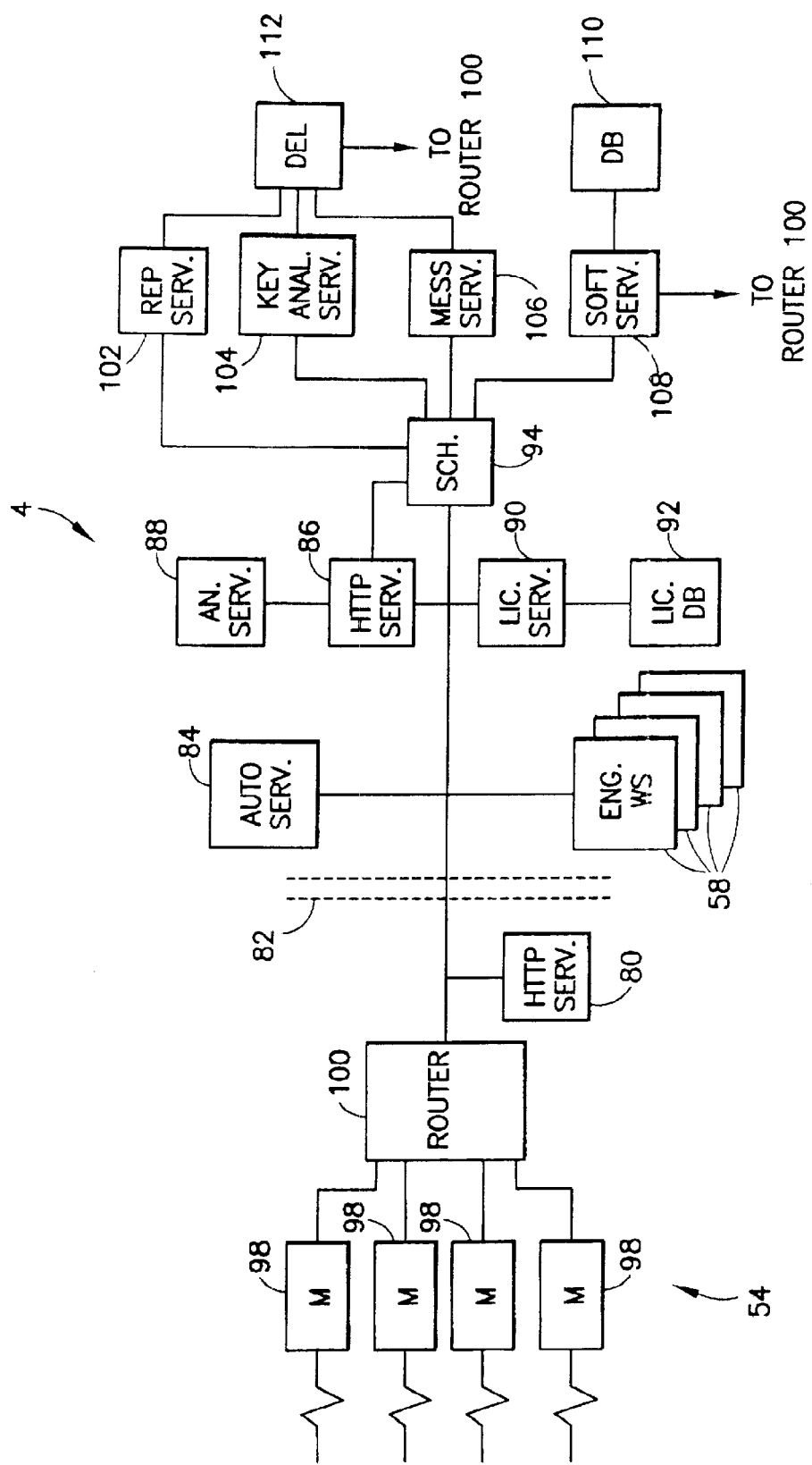
FIG. 8 is a block diagram of certain functional components of an exemplary central service facility for rendering interactive centralized service to a plurality of remotely located medical diagnostic systems.

FIG. 8 illustrates exemplary functional components for a central service facility 4 capable of analyzing ultrasound imaging system keystroke data in accordance with the preferred embodiment disclosed above. This service facility 4 includes a modem rack comprising a plurality of modems 98 coupled to a router 100 for coordinating data communications with the service facility. A so-called "front office" HTTP service server 80 receives and directs incoming and outgoing transactions with the facility. Server 80 is coupled to the other components of the facility through a firewall 82 for system security. This firewall prevents unauthorized access to the service facility in a manner generally known in the art. In addition, operator workstations 58 are coupled to the port manager for handling service requests and transmitting messages and reports in response to such requests. An automated service unit 84 may also be included in the service facility for automatically responding to certain service requests, sweeping subscribing diagnostic systems for keystroke data, etc. The automated service unit 84 may operate independently of or in conjunction with the interactive service components comprising processing system 56.

Behind firewall 82, a so-called "back office" HTTP application server 86 coordinates handling of service requests, keystroke analysis, messaging, reporting, software transfers, etc. Other servers may be coupled to HTTP application server 86, such as service analysis server 88 configured to address specific types of service requests. In the illustrated embodiment, processing system 56 also includes a license server 90 which is coupled to a license database 92 for storing, updating and verifying the status of ultrasound imaging system service subscriptions. Handling of service requests, messaging, and reporting is coordinated by a scheduler module 94 coupled to HTTP server 86. Scheduler module 94 coordinates activities of other servers comprising the processing system, such as a report server 102, a keystroke analysis server 104, a message server 106, and a software download server 108. As will be appreciated by those skilled in the art, servers 102, 104, 106, and 108 are coupled to memory devices (not shown) for storing data such as addresses, keystroke data log files, billing files, message and report files, applications software, etc. Software server 108 is coupled via one or more data channels to a storage device 110 for containing transmittable software packages which may be sent directly to the diagnostic systems, accessed by the diagnostic systems, or supplied on pay-per-use or purchase basis. Report and message servers 102 and 106 are further coupled to a delivery handling module 112, which is configured to receive outgoing messages, ensure proper connectivity with remote systems, and coordinate transmission of messages and reports to remote facilities via the network.

In accordance with the preferred embodiment of the invention, the keystroke analysis server 104 receives keystroke data from a remote imaging system via the scheduler module 94. The keystroke analysis server then performs the data acquisition, data conversion, data aggregation and data mining steps previously described. Based on the results of the keystroke analysis, appropriate departmental performance reports can be generated by report server 102 and downloaded to the remote ultrasound imaging system or to an administrative office at the remote facility via delivery handling module 112. In addition, the report server could be programmed with billing capability for generating bills based on ultrasound imaging system usage as determined by the keystroke analysis server. Alternatively, keystroke analysis and departmental performance report or bill generation can be controlled by service personnel interacting with a workstation at the service facility.

The foregoing functional circuitry may be configured as hardware, firmware, or software on any appropriate computer platform. For example, the functional circuitry of the imaging systems may be programmed as appropriate code in a personal computer or workstation, either incorporated entirely in or added to the system scanner. The functional circuitry of the service facility may include additional personal computers or workstations, in addition to a main frame computer in which one or more of the servers, the scheduler, etc. are configured. It should be noted that the web server 64 included in the uniform platform shown in FIG. 7 includes unique system identification data which supplements the information input by the user. The unique system identification data is automatically sent to the service center along with the keystroke data log file, thereby enabling the service facility to determine what types of reports, if any, that the remote facility is authorized to receive.

In accordance with a further aspect of the invention, the service facility may sweep a selected set of ultrasound imaging systems for the keystroke data stored in electronic memory in the system controllers. As used herein, the term "sweep" refers generally to a process of connecting system components, such as via a network connection, identifying desired data, and transmitting the data, either in an "upload" or a "download" scenario, depending upon the nature of the data and its use in servicing a system. Such sweeps may occur on regularly scheduled bases, at desired times (e.g., at off-peak utilization times) or on demand by a system user or a system application.

In accordance with an alternative preferred embodiment, the keystroke analysis algorithm disclosed herein could be embedded in the system controller of the remote ultrasound imaging system. There are, however, limitations on available processing power and the ability to compare the keystroke analysis results with the results of other systems.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "keystroke" means an act of any one of the following types: operation of input devices on the operator interface or on a probe, the selection of menu items on a graphical user interface, as well as the act of plugging in a probe or lifting a probe off of its yoke.

What is claimed is:

1. A method for analyzing use of a medical diagnostic system, comprising the steps of:
   automatically electronically storing keystroke data in machine-readable form from the time when power is turned on until the time when power is turned off, said keystroke data comprising encoded physical characteristics, encoded logical characteristics and an encoded time stamp for each and every keystroke input by a system operator while power is on;
   stripping said encoded physical characteristics out of said keystroke data; and
   mining said keystroke data remaining after said stripping step.

2. The method as recited in claim 1, further comprising the step of converting said keystroke data into human-readable form.

3. The method as recited in claim 1, wherein said mining step comprises the step of grouping said keystroke data.

4. The method as recited in claim 1, wherein said mining step comprises the step of testing for relationships in said keystroke data.

5. The method as recited in claim 1, wherein said mining step comprises the step of characterizing said keystroke data.

6. The method as recited in claim 1, wherein said step of electronic storage is performed in the medical diagnostic system, further comprising the step of transferring said keystroke data from said medical diagnostic system to an external computational platform.

7. The method as recited in claim 6, wherein said transferring step is performed via a network.

8. The method as recited in claim 7, wherein said steps of stripping and mining are performed at a central service facility.

9. The method as recited in claim 6, wherein said transferring step comprises the step of transferring said keystroke data from said hard disk to a portable disk.

10. The method as recited in claim 1, further comprising the step of aggregating keystroke data from multiple log files.

11. A system comprising a central service facility connected to a multiplicity of remotely located medical diagnostic systems via a network, wherein each of said medical diagnostic systems comprises:
    means for inputting keystrokes;
    means for automatically electronically storing keystroke data in machine-readable form from the time when power is turned on until the time when power is turned off, said keystroke data comprising encoded physical characteristics, encoded logical characteristics and an encoded time stamp for each and every keystroke input by a system operator while power is on; and
    means for transmitting said keystroke data to said network addressed to said service facility, and
    wherein said service facility comprises:
       means for receiving said keystroke data via said network;
       means for stripping said encoded physical characteristics out of said keystroke data; and
       means for mining said keystroke data remaining after said stripping.

12. The system as recited in claim 11, wherein said mining means comprise a software tool for sorting said keystroke data.

13. The system as recited in claim 11, wherein said mining means comprise a software tool for filtering said keystroke data.

14. The system as recited in claim 11, wherein said mining means comprise a software tool for characterizing said keystroke data.

15. The system as recited in claim 11, wherein said mining means comprise a software tool for determining the duration of an exam based on said keystroke data.

16. The system as recited in claim 11, further comprising means for aggregating keystroke data from multiple log files.

17. A system comprising a data processor connected to a medical diagnostic system via a network, wherein said medical diagnostic system comprises:
   means for inputting keystrokes;
   means for automatically electronically storing keystroke data in machine-readable form from the time when power is turned on until the time when power is turned off, said keystroke data comprising encoded physical characteristics, encoded logical characteristics and an encoded time stamp for each and every keystroke input by a system operator while power is on; and
   means for transmitting said keystroke data to said network addressed to said data processor, and
   wherein said data processor is programmed to perform the following steps:
      receiving said keystroke data via said network;
      stripping said encoded physical characteristics out of said keystroke data; and
      mining said keystroke data remaining after said stripping.

18. The system as recited in claim 17, wherein said mining step comprises the step of grouping said keystroke data.

19. The system as recited in claim 17, wherein said mining step comprises the step of testing for relationships in said keystroke data.

20. The system as recited in claim 17, wherein said mining step comprises the step of characterizing said keystroke data.

21. The system as recited in claim 17, wherein said mining step comprises the step of determining the duration of an exam based on said keystroke data.

22. The system as recited in claim 17, further comprising a probe and a yoke on which said probe can be hooked, wherein said means for inputting keystrokes comprises a switch which is activated when said probe is removed from said yoke.

23. The system as recited in claim 17, wherein said means for inputting keystrokes comprises a power-on switch.

24. The system as recited in claim 17, wherein said means for inputting keystrokes comprise input buttons on a control panel.

25. The system as recited in claim 17, wherein said means for inputting keystrokes comprise virtual buttons on a graphical interface.

26. The system as recited in claim 17, further comprising a probe, wherein said means for inputting keystrokes comprise a switch on said probe.

27. A system comprising a data processor connected to a medical diagnostic system via a network, wherein said medical diagnostic system comprises:
   an operator interface for inputting keystrokes;
   means for encoding each and every one of said keystrokes while power is on to form encoded keystroke data in response to keystroke input, wherein said encoded keystroke data comprises a time stamp and an identifier for each keystroke;
   electronic memory for storing said encoded keystroke data;
   means for automatically storing said encoded keystroke data in said electronic memory in response to each and every keystroke input while power is on; and
   means for transmitting said keystroke data to said network addressed to said data processor, and
   wherein said data processor is programmed to perform the following steps:
      receiving said keystroke data via said network; and
      analyzing said keystroke data.

28. The system as recited in claim 27, further comprising means for generating a departmental performance analysis report based on the results of said analyzing step.

29. The system as recited in claim 27, further comprising means for generating a bill for medical diagnostic system usage based on the results of said analyzing step.

30. The system as recited in claim 27, wherein said analyzing step comprises the step of grouping said keystroke data.

31. The system as recited in claim 27, wherein said analyzing step comprises the step of testing for relationships in said keystroke data.

32. The system as recited in claim 27, wherein said analyzing step comprises the step of characterizing said keystroke data.

33. The system as recited in claim 27, wherein said analyzing step comprises the step of determining the duration of an exam based on said keystroke data.

34. The system as recited in claim 27, wherein said medical diagnostic system is an ultrasound imaging system.

35. A method for analyzing use of a medical diagnostic system, comprising the steps of:
   encoding each and every keystroke while power to said system is on to form encoded keystroke data, wherein said encoded keystroke data comprises a time stamp and an identifier for each keystroke;
   automatically storing said encoded keystroke data in response to keystroke input while said power is on;
   retrieving said stored keystroke data from storage; and
   analyzing said retrieved keystroke data.

36. The method as recited in claim 35, further comprising the step of generating a departmental performance analysis report based on the results of said analyzing step.

37. The method as recited in claim 35, wherein said analyzing step comprises the step of grouping said keystroke data.

38. The method as recited in claim 35, wherein said analyzing step comprises the step of testing for relationships in said keystroke data.

39. The method as recited in claim 35, wherein said analyzing step comprises the step of characterizing said keystroke data.

40. The method as recited in claim 35, wherein said analyzing step comprises the step of determining the duration of an exam based on said keystroke data.

41. A medical diagnostic system comprising:
   an operator interface for inputting keystrokes;
   means for encoding said keystrokes to form each and every one of said keystrokes while power is on encoded keystroke data in response to keystroke input, wherein said keystroke data comprises a time stamp and an identifier for each keystroke;
   electronic memory for storing said encoded keystroke data;

means for automatically storing said encoded keystroke data in said memory in response to each and every keystroke input while power is on; and a data processor programmed to analyze said stored keystroke data.

42. The system as recited in claim 41, further comprising means for generating a departmental performance analysis report based on the results of said analysis of said keystroke data.

43. The system as recited in claim 41, further comprising an ultrasound signal processing subsystem, a display monitor for viewing ultrasound images, and an ultrasound transducer probe coupled to said ultrasound signal processing system.

\* \* \* \* \*